United States Patent
Pillai

(10) Patent No.: US 9,915,580 B2
(45) Date of Patent: Mar. 13, 2018

(54) PULP CHAMBER LEAK TEST

(71) Applicant: Colgate-Palmolive Company, New York, NY (US)

(72) Inventor: Shyamala Pillai, Hillsborough, NJ (US)

(73) Assignee: Colgate-Palmolive Company, New York, NY (US)

( * ) Notice: Subject to any disclaimer, the term of this patent is extended or adjusted under 35 U.S.C. 154(b) by 58 days.

(21) Appl. No.: 15/027,583

(22) PCT Filed: Oct. 8, 2013

(86) PCT No.: PCT/US2013/063901
§ 371 (c)(1),
(2) Date: Apr. 6, 2016

(87) PCT Pub. No.: WO2015/053754
PCT Pub. Date: Apr. 16, 2015

(65) Prior Publication Data
US 2016/0245717 A1    Aug. 25, 2016

(51) Int. Cl.
*G01M 3/06* (2006.01)
*A61C 19/04* (2006.01)

(52) U.S. Cl.
CPC .............. *G01M 3/06* (2013.01); *A61C 19/04* (2013.01)

(58) Field of Classification Search
CPC .................................. G01M 3/06; A61C 19/04
See application file for complete search history.

(56) References Cited

U.S. PATENT DOCUMENTS 2,107,922 A  *  2/1938  Westin ................ G01M 3/3218
                                                        285/333
5,170,658 A      12/1992  Thayer

OTHER PUBLICATIONS

Ferreira et al., 2008, "Marginal Leakage in Direct and Indirect Composite Resin Restorations in Primary Teeth: An in vitro Study," Journal of Dentistry 36(5):322-325.
International Search Report and Written Opinion of the ISA in International Application No. PCT/US2013/063901, dated Jun. 17, 2014.
Taylor et al., 1992, "Microleakage," Journal of Dentistry 20(1):3-10.
Xu et al., 2005, "A New Quantitative Method Using Glucose for Analysis of Endontie Leakage," Oral Surgery, Oral Medicine, Oral Pathology, Oral Radiology and Endodontics 99(1):107-111.
Yared et al., 1996, "Sealing Ability of the Vertical Condensation with Different Root Canal Sealers," Journal of Endodontics 22(1):6-8.

\* cited by examiner

*Primary Examiner* — Nguyen Ha

(57) ABSTRACT

A method of testing for leakage of a pulp chamber in a modified extracted tooth is provided, wherein the modified extracted tooth comprises enamel, dentine and a pulp chamber. The method comprises: (a) providing an extracted tooth which has been modified by removal of roots and dental pulp so as to create a pulp chamber, the pulp chamber having an opening at one end thereof, which opening is defined by a rim; (b) attaching a first end of a first tube to the rim of the pulp chamber so as to provide an air-tight seal between the first tube and the rim; (c) placing the modified extracted tooth into a liquid; (d) supplying a compressed gas into the pulp chamber via the first tube; and (e) determining visually whether or not bubbles of the gas are released into the liquid at the enamel of the tooth.

17 Claims, 3 Drawing Sheets

PULP CHAMBER LEAK TEST

BACKGROUND

Pulp chamber models are used to study diffusion of various actives (such as, for example, peroxides and peracetic acid) through the enamel of a tooth into the dentine layer. A pulp chamber model is made from an extracted tooth, from which the roots and dental pulp have been removed so as to form a pulp chamber.

Whilst undertaking such studies, it is very important to ensure that the pulp chamber models used do not have any leaks in the enamel thereof which would allow the actives to seep into the pulp chamber, as this would give false positive results (i.e. a result of an active apparently diffusing through the enamel, when it has in fact merely entered the dentin through e.g. a fracture or hole in the enamel). However, it has previously been very difficult to determine whether or not a pulp chamber model has such leaks, and no reliable method of determining whether or not a pulp chamber model has leaks in the enamel thereof has previously been devised.

It would therefore be desirable to provide a methodology for verifying that the pulp chamber models used in the above studies are of good quality i.e. do not have leaks in the enamel, thus avoiding generation of false positive results.

SUMMARY

A first aspect of the present invention provides a method of testing for leakage of a pulp chamber in a modified extracted tooth, the modified extracted tooth comprising enamel, dentine and a pulp chamber; the method comprising:

(a) providing an extracted tooth which has been modified by removal of roots and dental pulp so as to create a pulp chamber, the pulp chamber having an opening at one end thereof, which opening is defined by a rim;

(b) attaching a first end of a first tube to the rim of the pulp chamber so as to provide an air-tight seal between the first tube and the rim;

(c) placing the modified extracted tooth into a liquid;

(d) supplying a compressed gas into the pulp chamber via the first tube; and (e) determining visually whether or not bubbles of the gas are released into the liquid at the enamel of the tooth.

Optionally, the extracted tooth has been further modified by removal of at least a portion of the dentine so as to increase the volume of the pulp chamber.

Optionally, the compressed gas is supplied into the pulp chamber at a pressure of between 3 psi and 12 psi (between 20.6 kPa and 82.7 kPa)

Optionally, the compressed gas is supplied into the pulp chamber at a pressure of between 5 psi and 10 psi (between 34.5 kPa and 68.9 kPa).

Optionally, the compressed gas is supplied into the pulp chamber at a pressure of between 6 psi and 9 psi (between 41.4 kPa and 62.1 kPa).

Optionally, the compressed gas is supplied into the pulp chamber at a pressure of between 7 psi and 8 psi (between 48.3 kPa and 55.1 kPa).

Optionally, the compressed gas is supplied to the pulp chamber in step (d) for a period of at least 20 seconds.

Optionally, the compressed gas is supplied to the pulp chamber in step (d) for a period of between 30 seconds and 1 minute.

Optionally, the first end of the first tube is attached to the rim of the pulp chamber with an adhesive.

Optionally, in step (b), an O-ring is attached to the rim of the pulp chamber and the first end of the first tube is attached to the O-ring. Optionally, the rim of the pulp chamber and the first end of the first tube are attached to the O-ring with an adhesive.

Optionally, the compressed gas is compressed air.

Optionally, the liquid is water.

Optionally, the extracted tooth is an extracted molar.

Optionally, the extracted tooth is an extracted human molar.

Optionally, at any time before step (d), the method further comprises the steps of: (i) attaching a second end of the first tube to an outlet valve of a pressure gauge; and (ii) attaching an inlet valve of the pressure gauge to a supply of the compressed gas.

Optionally, the outlet valve is closed and, immediately before step (d), the method further comprises the step of supplying the compressed gas to the inlet valve of the pressure gauge; wherein the supplying of the compressed gas into the pulp chamber in step (d) comprises the step of opening the outlet valve of the pressure gauge; and wherein the method further comprises monitoring the pressure as shown on the pressure gauge from when the compressed gas is supplied to the inlet valve of the pressure gauge.

Optionally, the inlet valve of the pressure gauge is connected to the supply of compressed gas by a second tube.

DETAILED DESCRIPTION

Figure 1:
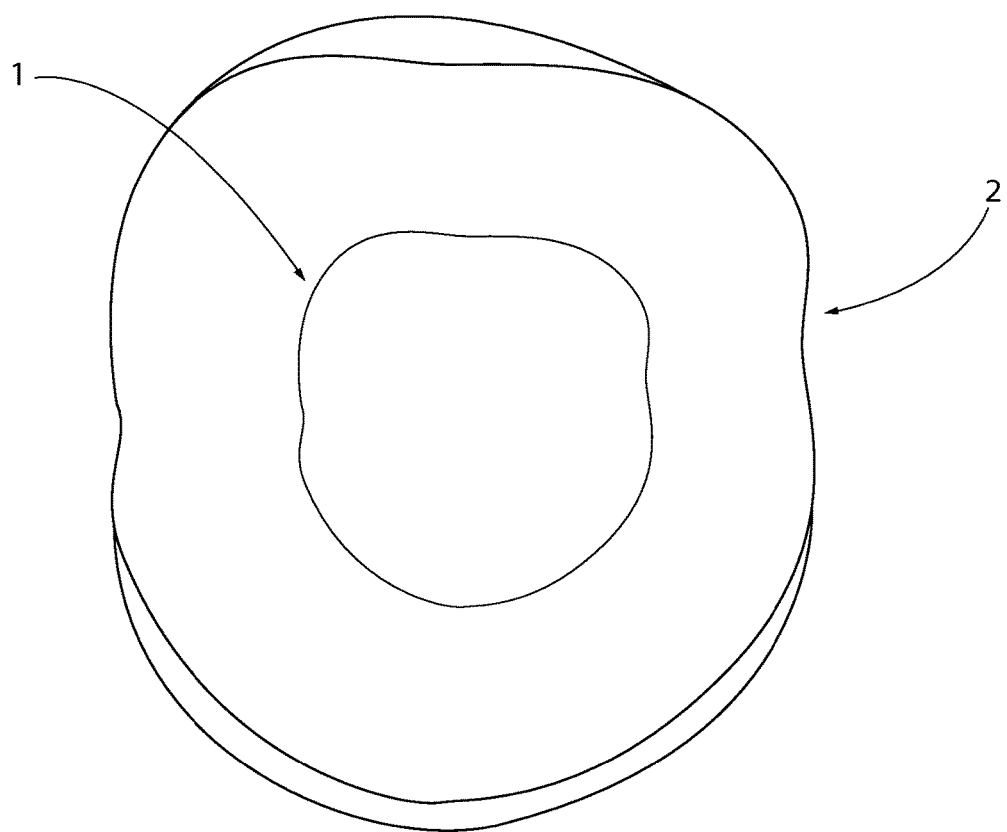
FIG. 1 shows a pulp chamber model formed from an extracted tooth from which the roots, dental pulp and some of the dentin have been removed so as to create a pulp chamber.

The following description of the preferred embodiments is merely exemplary in nature and is in no way intended to limit the invention, its application, or uses.

As used throughout, ranges are used as shorthand for describing each and every value that is within the range. Any value within the range can be selected as the terminus of the range.

All references cited herein are hereby incorporated by reference in their entireties. In the event of a conflict in a definition in the present disclosure and that of a cited reference, the present disclosure controls.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the term "about", when applied to the value for a parameter of a method of this invention, indicates that the calculation or the measurement of the value allows some slight imprecision without having a substantial effect on the attributes of the method. If, for some reason, the imprecision provided by "about" is not otherwise understood in the art with this ordinary meaning, then "about" as used herein indicates a possible variation of up to 5% in the value.

As used herein, numerical values of pressure relate to the pressure relative to ambient atmospheric pressure, rather than the pressure relative to a vacuum. References to psi (pounds per square inch) should therefore be taken to be references to psig (pounds per square inch gauge) unless otherwise specified. Unless otherwise indicated, all methods and examples disclosed herein were carried out at ambient temperature of 25° C.

The description of illustrative embodiments according to principles of the present invention is intended to be read in connection with the accompanying drawings, which are to be considered part of the entire written description.

In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise.

Moreover, the features and benefits of the invention are illustrated by reference to the preferred embodiments. Accordingly, the invention expressly should not be limited to such preferred embodiments illustrating some possible non-limiting combination of features that may exist alone or in other combinations of features.

The present inventors have developed a methodology for verifying that pulp chamber models used in studies of diffusion of actives through enamel to dentin are of good quality with no leaks in the enamel. Pulp chamber models can thus be checked for leaks and holes which are not immediately apparent upon visual inspection of the extracted tooth. The method thus provides for the avoidance of false positive results, and allows for the provision of more accurate data in studies carried out using the pulp chamber models, as it is possible to identify pulp chamber models which are of suitable quality for use in such studies.

In a first aspect, there is provided a method of testing for leakage of a pulp chamber in a modified extracted tooth, the modified extracted tooth comprising enamel, dentine and a pulp chamber; the method comprising:

(a) providing an extracted tooth which has been modified by removal of roots and dental pulp so as to create a pulp chamber, the pulp chamber having an opening at one end thereof, which opening is defined by a rim;

(b) attaching a first end of a first tube to the rim of the pulp chamber so as to provide an air-tight seal between the first tube and the rim;

(c) placing the modified extracted tooth into a liquid;

(d) supplying a compressed gas into the pulp chamber via the first tube; and (e) determining visually whether or not bubbles of the gas are released into the liquid at the enamel of the tooth.

If the pulp chamber model does not contain any leaks, then then no bubbles of gas will be released into the liquid at the enamel of the modified extracted tooth. However, if the pulp chamber model does contain leaks, then bubbles of gas will be released into the liquid at the enamel of the modified extracted tooth.

A pulp chamber model is made from an extracted tooth, from which the roots and dental pulp have been removed so as to form a pulp chamber 1. In some embodiments, and as illustrated in FIG. 1, the modified extracted tooth 2 used in the methods of the present invention has been further modified by removal of at least a portion of the dentine so as to increase the volume of the pulp chamber 1. Typically, dental saws and drills are used to cut off the roots and to remove the dentine. It may be desirable to remove as much of the dentine as is possible. In certain pulp chamber models which may be used in the method of the present invention, less than 20% by volume, less than 15% by volume, less than 10% by volume, from 5 to 15% by volume, from 7 to 12% by volume, or about 10% by volume of the dentine has been removed, relative to the amount of dentine which was present immediately following removal of the roots and the dental pulp from the extracted tooth.

In some embodiments, the extracted tooth is an extracted molar. In some embodiments, the extracted tooth is an extracted human molar.

In certain embodiments, the compressed gas supplied to the pulp chamber at a pressure of between 3 psi and 12 psi (between 20.6 kPa and 82.7 kPa), between 5 psi and 10 psi (between 34.5 kPa and 68.9 kPa), between 6 psi and 9 psi (between 41.4 kPa and 62.1 kPa), or between 7 psi and 8 psi (between 48.3 kPa and 55.1 kPa).

In some embodiments, the compressed gas is supplied to the pulp chamber in step (d) for a period of at least 20 seconds. In some embodiments, the compressed gas is supplied to the pulp chamber in step (d) for a period of between 30 seconds and 1 minute.

In one embodiment, the first end of the first tube is attached to the rim of the pulp chamber with an adhesive. In certain embodiments, the adhesive is an epoxy adhesive.

In one embodiment, an O-ring is attached to the rim of the pulp chamber and the first end of the first tube is attached to the O-ring. In some embodiments, the rim of the pulp chamber and the first end of the first tube are attached to the O-ring with an adhesive, which may be an epoxy adhesive (as above). In certain embodiments, when an epoxy adhesive is used to attach the O-ring to the rim of the pulp chamber, the adhesive is allowed to dry for between about 5 and 10 minutes before attaching the first end of the first tube to the O-ring.

In certain embodiments, the first tube has a length of between about 6 inches and 24 inches (15.2 cm and 61.0 cm), between about 8 inches and 18 inches (20.3 cm and 45.7 cm), between about 10 inches and 14 inches (25.4 cm and 35.6 cm), or of about 12 inches (30.5 cm).

In certain embodiments, the compressed gas is compressed air. Other compressed gases which may be used in the methods of the present invention include, but are not limited to, nitrogen.

In certain embodiments, the liquid in step (c) is water. Other liquids which may be used in the methods of the present invention include, but are not limited to, saliva, a buffer solution, or a mixture of saliva and water.

In certain embodiments, at any time before step (d), the method further comprises the steps of: (i) attaching a second end of the first tube to an outlet valve of a pressure gauge;

and (ii) attaching an inlet valve of the pressure gauge to a supply of the compressed gas.

In certain embodiments, the outlet valve is closed and, immediately before step (d), the method further comprises the step of supplying the compressed gas to the inlet valve of the pressure gauge; wherein the supplying of the compressed gas into the pulp chamber in step (d) comprises the step of opening the outlet valve of the pressure gauge; and wherein the method further comprises monitoring the pressure as shown on the pressure gauge from when the compressed gas is supplied to the inlet valve of the pressure gauge. If the pulp chamber model does not contain any leaks then, upon opening of the outlet valve, the pressure reading on the pressure gauge undergoes an initial slight decrease from the value measured before the outlet valve was opened (as, with the outlet valve closed, the pressure in the first tube and pulp cavity is less than that in the second tube and pressure gauge, therefore a slight decrease in the pressure reading on the gauge is seen as the outlet vale is opened and the compressed gas enters the first tube and pulp cavity), following which decrease the pressure reading then increases again to the value measured before the outlet valve was opened, at which value it then remains constant (as the compressed gas continues to be supplied into the pulp chamber once the outlet valve has been opened). This indicates that the pulp chamber is robust and does not have any cracks or lesions through which the compressed gas could escape. However, if the pulp chamber model does contain leaks then, upon opening of the outlet valve, the pressure reading on the pressure gauge decreases and continues to decrease rapidly, rather than increasing again to the value as measured on the pressure gauge when the outlet valve was closed. This indicates loss of the gas through such minute cracks or lesions/holes in the pulp chamber model. Also, if the pulp chamber model does contain leaks, then a stream of bubbles is observed in the liquid, indicating that the compressed gas is able to escape through such minute cracks.

In certain embodiments, the inlet valve of the pressure gauge is connected to the supply of compressed gas by a second tube. In certain embodiments, the second tube has a length of between about 6 inches and 24 inches (15.2 cm and 61.0 cm), between about 8 inches and 18 inches (20.3 cm and 45.7 cm), between about 10 inches and 14 inches (25.4 cm and 35.6 cm), or of about 12 inches (30.5 cm).

According to an embodiment of the method of the present invention, a pulp chamber formed from an extracted human molar was tested for leaks. The pulp chamber had been formed by cutting off the roots of the molar and removing the dental pulp and approximately 10% by volume of the dentine (relative to the amount of dentine which was present immediately following removal of the roots and the dental pulp). The pulp chamber 1 of the modified extracted tooth 2 is illustrated in FIG. 1.

Figure 2:
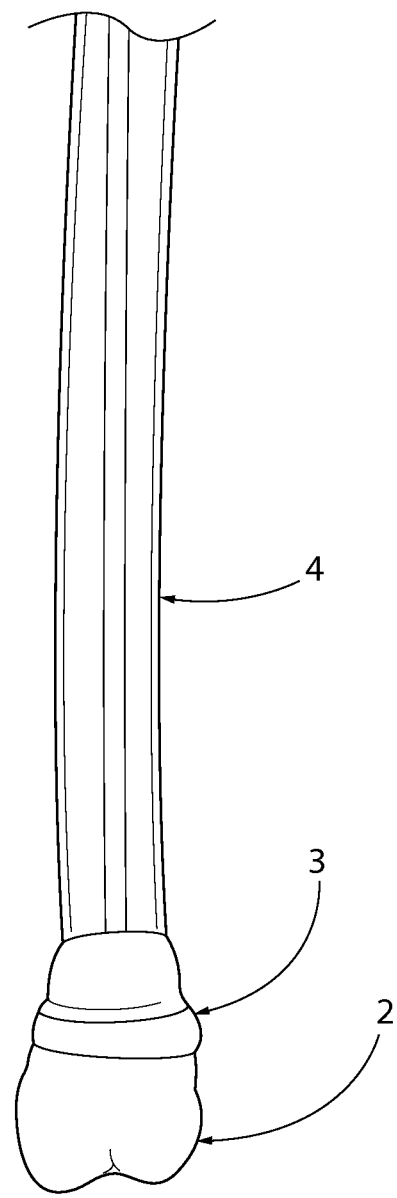
FIG. 2 shows a pulp chamber to which a tube has been attached via an O-ring.

An O-ring 3 was then attached to the rim of the pulp chamber using an epoxy glue. Contact of the glue with the enamel of the modified extracted tooth 2 was avoided. The glue was allowed to dry for at least 5 to 10 minutes. One end of a tube 4, which tube 4 was approximately 12 inches (30.5 cm) in length, was then attached to the O-ring 3 using a glue and allowed to air-dry fully. The extracted modified tooth 2 with the tube 4 so attached is illustrated in FIG. 2.

Figure 3:
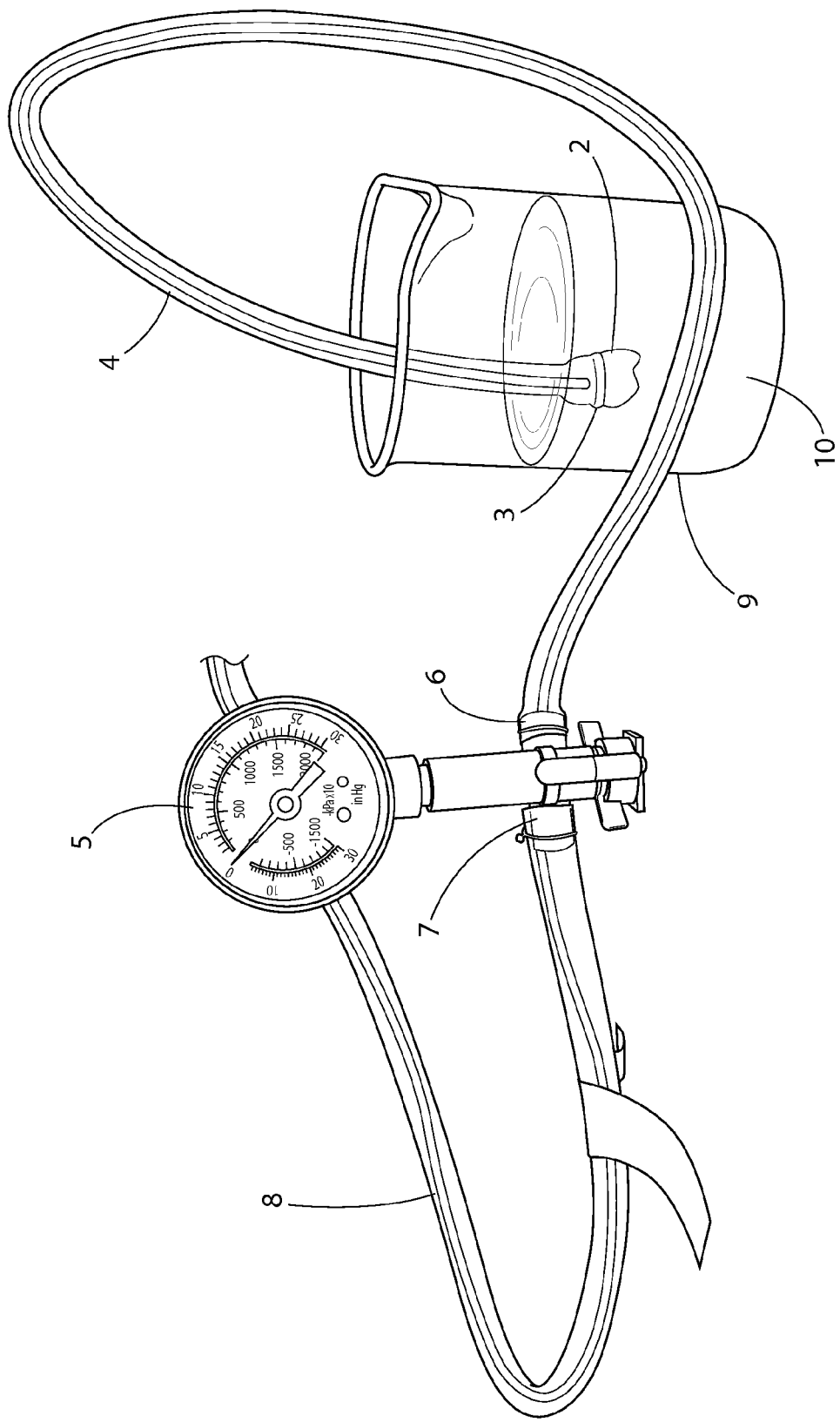
FIG. 3 shows an example of an apparatus used in an embodiment of the method of the present invention.

As illustrated in FIG. 3, with the pulp chamber rim attached to the tube 4 via the O-ring 3 (and with no visible leaks observed), the other end of the tube 4 was attached to the outlet valve 6 of a pressure gauge 5. The outlet valve 6 was closed. An inlet valve 7 of the pressure gauge 5 was attached to a supply of compressed air (not shown) using a second tube 8 (with the supply of compressed air remaining switched off at this point). The modified extracted tooth 2 was placed in a beaker 9 containing water 10. The compressed air supply was then switched on, and air was allowed to build up in the second tube 8 (i.e. the tube connecting the air supply to the inlet valve 7 of the pressure gauge 5) at a pressure of 5 to 10 psi (34.5 kPa to 68.9 kPa). The outlet valve 6 of the pressure gauge 5 was then opened to allow the air to flow to the pulp chamber 1.

With the outlet valve 6 opened, the pressure reading on the pressure gauge 5 was seen to remain constant. In the beaker 9 of water 10 it was observed that there were no bubbles coming from the tooth 2. These results thus show that the pulp chamber did not have any leaks.

The above process was then repeated using a modified extracted tooth which contained a visible dental cavity. In this experiment, the pressure did not remain constant upon opening of the outlet valve and, in the beaker of water, bubbles could be seen coming from the cavity of the tooth. This showed that the pulp chamber of the modified extracted tooth was leaking, as expected for a tooth containing a dental cavity.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the scope of the invention should be construed broadly as set forth in the appended claims.

I claim:

1. A method of testing for leakage of a pulp chamber in a modified extracted tooth, the modified extracted tooth comprising enamel, dentine and a pulp chamber; the method comprising:
    (a) providing an extracted tooth which has been modified by removal of roots and dental pulp so as to create a pulp chamber, the pulp chamber having an opening at one end thereof, which opening is defined by a rim;
    (b) attaching a first end of a first tube to the rim of the pulp chamber so as to provide an air-tight seal between the first tube and the rim;
    (c) placing the modified extracted tooth into a liquid;
    (d) supplying a compressed gas into the pulp chamber via the first tube; and
    (e) determining visually whether or not bubbles of the gas are released into the liquid at the enamel of the tooth,
wherein the extracted tooth has been further modified by removal of at least a portion of the dentine so as to increase the volume of the pulp chamber.

2. The method of claim 1, wherein the compressed gas is supplied into the pulp chamber at a pressure of between 3 psi and 12 psi (between 20.6 kPa and 82.7 kPa).

3. The method of claim 2, wherein the compressed gas is supplied into the pulp chamber at a pressure of between 5 psi and 10 psi (between 34.5 kPa and 68.9 kPa).

4. The method of claim 3, wherein the compressed gas is supplied into the pulp chamber at a pressure of between 6 psi and 9 psi (between 41.4 kPa and 62.1 kPa).

5. The method of claim 4, wherein the compressed gas is supplied into the pulp chamber at a pressure of between 7 psi and 8 psi (between 48.3 kPa and 55.1 kPa).

6. The method of claim 1, wherein the compressed gas is supplied to the pulp chamber in step (d) for a period of at least 20 seconds.

7. The method of claim 6, wherein the compressed gas is supplied to the pulp chamber in step (d) for a period of between 30 seconds and 1 minute.

8. The method of claim 1, wherein the first end of the first tube is attached to the rim of the pulp chamber with an adhesive.

9. The method of claim 1 wherein, in step (b), an O-ring is attached to the rim of the pulp chamber and the first end of the first tube is attached to the O-ring.

10. The method of claim 9, wherein the rim of the pulp chamber and the first end of the first tube are attached to the O-ring with an adhesive.

11. The method of claim 1, wherein the compressed gas is compressed air.

12. The method of claim 1, wherein the liquid is water.

13. The method of claim 1 wherein the extracted tooth is an extracted molar.

14. The method of claim 13 wherein the extracted tooth is an extracted human molar.

15. The method of claim 1 wherein, at any time before step (d), the method further comprises the steps of:
 (i) attaching a second end of the first tube to an outlet valve of a pressure gauge; and
 (ii) attaching an inlet valve of the pressure gauge to a supply of the compressed gas.

16. The method of claim 15 wherein the outlet valve is closed and, immediately before step (d), the method further comprises the step of supplying the compressed gas to the inlet valve of the pressure gauge;
 wherein the supplying of the compressed gas into the pulp chamber in step (d) comprises the step of opening the outlet valve of the pressure gauge; and wherein the method further comprises monitoring the pressure as shown on the pressure gauge from when the compressed gas is supplied to the inlet valve of the pressure gauge.

17. The method of claim 15, wherein the inlet valve of the pressure gauge is connected to the supply of compressed gas by a second tube.

* * * * *